(12) United States Patent
Li et al.

(10) Patent No.: US 11,059,230 B2
(45) Date of Patent: Jul. 13, 2021

(54) BIOMATERIAL PRINTING APPARATUS

(71) Applicant: Industrial Technology Research Institute, Hsinchu (TW)

(72) Inventors: Chang-Chou Li, Tainan (TW); Li-Wen Lai, Tainan (TW); Yang-Cheng Lin, Chiayi (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 408 days.

(21) Appl. No.: 16/262,346

(22) Filed: Jan. 30, 2019

(65) Prior Publication Data

US 2020/0079024 A1 Mar. 12, 2020

(30) Foreign Application Priority Data

Sep. 10, 2018 (TW) ................. 107131662

(51) Int. Cl.
*B29C 64/393* (2017.01)
*A61L 27/60* (2006.01)
(Continued)

(52) U.S. Cl.
CPC ........ *B29C 64/393* (2017.08); *A61L 27/3604* (2013.01); *A61L 27/60* (2013.01);
(Continued)

(58) Field of Classification Search
CPC .............................. B29C 64/20; B29C 64/393
See application file for complete search history.

(56) References Cited

U.S. PATENT DOCUMENTS 8,931,880 B2 1/2015 Murphy et al.
9,514,397 B2 12/2016 Peek
(Continued)

FOREIGN PATENT DOCUMENTS

CN 204585850 U 8/2015
CN 105496601 A 4/2016
(Continued)

OTHER PUBLICATIONS

Kikuchi et al., "Automatic fabrication of 3-dimensional tissues using cell sheet manipulator technique," Biomaterials, Dec. 23, 2013, pp. 2428-2435.
(Continued)

*Primary Examiner* — James Sanders
(74) *Attorney, Agent, or Firm* — Birch, Stewart, Kolasch & Birch, LLP

(57) ABSTRACT

A biomaterial printing apparatus includes a support base, a movement device, a printing device, a first optical-detection device, and a second optical-detection device. The carrier is configured for a culture container to be put thereon. The movement device is connected to the support base. The printing device is connected to the movement device. The first optical-detection device is configured to detect the position of the injection needle of the printing device. The second optical-detection device is configured to detect the position of the culture container. According to the detection of the first optical-detection device and the second optical-detection device, the biological material printing device can accurately move the injection needle to the injection position relative to the culture container, thereby improving the accuracy of printing the biological material.

8 Claims, 15 Drawing Sheets

(51) Int. Cl.
  *A61L 27/36* (2006.01)
  *B29C 64/20* (2017.01)
  *B33Y 50/02* (2015.01)
  *B33Y 70/00* (2020.01)
  *B33Y 30/00* (2015.01)

(52) U.S. Cl.
  CPC .............. *B29C 64/20* (2017.08); *B33Y 30/00* (2014.12); *B33Y 50/02* (2014.12); *B33Y 70/00* (2014.12)

(56) References Cited

U.S. PATENT DOCUMENTS

| | | | |
|---|---|---|---|
| 9,545,302 B2 | 1/2017 | Tumey et al. | |
| 2015/0037445 A1* | 2/2015 | Murphy | C12M 33/00 425/131.1 |
| 2015/0375453 A1 | 12/2015 | Yost et al. | |
| 2017/0198252 A1 | 7/2017 | Mironov et al. | |

FOREIGN PATENT DOCUMENTS

| | | |
|---|---|---|
| CN | 20525537 U | 5/2016 |
| CN | 105659089 A | 6/2016 |
| CN | 103249567 B | 8/2016 |
| DE | 10 2014 214 944 A1 | 2/2016 |
| TW | 556858 | 1/1992 |
| TW | M487830 U | 10/2014 |
| WO | WO 2016/016271 A2 | 2/2016 |

OTHER PUBLICATIONS

Koch et al., "Skin Tissue Generation by Laser Cell Printing," Biotechnology & Bioengineering, Feb. 13, 2012, pp. 1855-1863.

Lee et al., "Design and Fabrication of Human Skin by Three-Dimensional Bioprinting," Tissue Engineering: part C, vol. 20, No. 6, 2014, pp. 473-484.

Taiwanese Office Action and Search Report, dated Mar. 13, 2019, for Taiwanese Application No. 107131662.

* cited by examiner

BIOMATERIAL PRINTING APPARATUS

CROSS-REFERENCE TO RELATED APPLICATIONS

This Application claims priority of Taiwan Patent Application No. 107131662 filed on Sep. 10, 2018, the entirety of which is incorporated by reference herein.

BACKGROUND

Field of the Invention

The present disclosure relates to a printing apparatus, and in particular to a biomaterial printing apparatus.

Description of the Related Art

Conventional bionic skin can be attached to a patient's wound to prevent the patient from dispersing water or preventing bacterial infection. The skin cells of the patient may be included in the current bionic skin. When the bionic skin is attached to the wound of the patient, the wound does not easily repel the bionic skin, and it can be well integrated into the wound of the patient. Therefore, there is no need to replace the bionic skin on a regular basis, and the bionic skin can greatly enhance the efficacy of treatment.

In addition, in the production of bionic skin, due to the use of active skin cells, skin cells can grow in the culture container, thereby reducing the time it takes to make bionic skin, in order to provide more immediate treatment for patients.

However, bionic skin is difficult to manufacture, and the yield is low, and thus the price of the bionic skin is very high, placing the burden on the patient. Accordingly, although existing bionic skin has generally been adequate for its intended purposes, it has not been entirely satisfactory in all respects. Consequently, it would be desirable to provide a solution for improving bionic skin.

BRIEF SUMMARY

The present disclosure provides a biomaterial printing apparatus, which can reduce the difficulty of fabricating a biomimetic product such as bionic skin, and can improve the yield of production, thereby reducing the manufacturing cost of the biomimetic product.

The present disclosure provides a biomaterial printing apparatus including a support base, at least one printing device, a movement device, a control device, a first optical-detection device, and a second optical-detection device. The support base is configured to have at least one culture container put on it. The printing device includes an injection needle configured for receiving biological materials. The movement device is configured to move the support base and the printing device. The control device is electrically connected to movement device and the printing device.

The first optical-detection device is electrically connected to the control device. The first optical-detection device is configured to detect the position of the injection needle, generate a first detection signal, and transmit the first detection signal to the control device. The second optical-detection device is electrically connected to the control device. The second optical-detection device is configured to detect the position of the culture container, generate a second detection signal, and transmit the second detection signal to the control device. The control device drives the movement device to move the injection needle to an injection position according to the first detection signal and the second detection signal, and drives the printing device to inject the biological material into the culture container via the injection needle.

The biomaterial printing apparatus of the present disclosure can produce a biomimetic product in a three-dimensional printing manner, thereby reducing the difficulty in the production of the biomimetic product. Moreover, the biomaterial printing apparatus of the present disclosure utilizes a variety of optical-detection devices, so that the injection needle can accurately inject the biological material into the culture container, thereby increasing the yield of the biomimetic product, and reducing the manufacturing cost of the biomimetic product.

BRIEF DESCRIPTION OF THE DRAWINGS

The invention can be more fully understood by reading the subsequent detailed description and examples with references made to the accompanying drawings, wherein.

DETAILED DESCRIPTION

Figure 1:
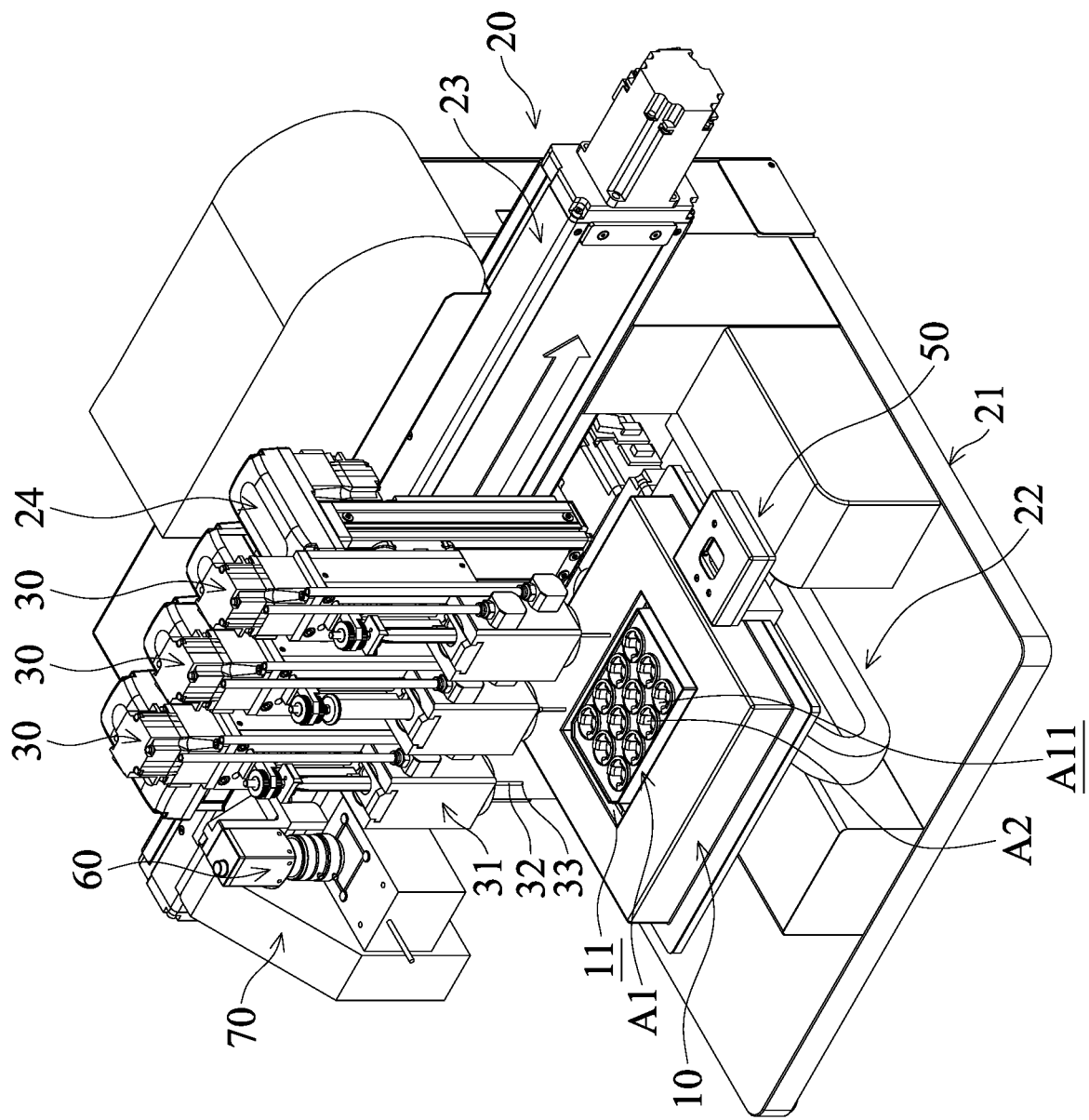
FIG. 1 is a perspective view of the biomaterial printing apparatus in accordance with some embodiments of the present disclosure.

The following disclosure provides many different embodiments, or examples, for implementing different features of the present disclosure. Specific examples of components and arrangements are described below to simplify the present disclosure. For example, the formation of a first feature over or on a second feature in the description that follows may include embodiments in which the first and second features are formed in direct contact, and may also include embodiments in which additional features may be formed between the first and second features, such that the first and second features may not be in direct contact.

The words, such as "first" or "second", in the specification are for the purpose of clarity of description only, and are not relative to the claims or meant to limit the scope of the claims. In addition, terms such as "first feature" and "second feature" do not indicate the same or different features.

Spatially relative terms, such as upper and lower, may be used herein for ease of description to describe one element or feature's relationship to other elements or features as illustrated in the figures. The spatially relative terms are intended to encompass different orientations of the device in use or operation in addition to the orientation depicted in the figures. Moreover, the shape, size, thickness, and angle of tilt depicted in the drawings may not be drawn to scale or may be simplified for clarity of discussion; these drawings are merely intended for illustration.

FIG. 1 is a perspective view of the biomaterial printing apparatus 1 in accordance with some embodiments of the present disclosure. The biomaterial printing apparatus 1 is configured to print a biological material in three dimensions to form a biomimetic product, such as bionic skin or bionic tissue.

The biomaterial printing apparatus 1 includes a support base 10, a movement device 20 and printing devices 30. The support base 10 is configured for a tray A1 and culture containers A2 to be put thereon. The support base 10 has a support groove 11. The tray A1 is configured to be put in the support groove 11. The support groove 11 is configured to limit the position of the tray A1 that is put on the support base 10, and configured to limit the movement of the tray A1 relative to the support base 10.

The tray A1 has receiving grooves A11. The receiving grooves A11 may be arranged on a horizontal plane in an array. The culture container A2 may be put in the receiving groove A11. The receiving groove A11 is configured to limit the position of the culture container A2 that is put on the tray A1, and configured to limit the movement of the culture container A2 relative to the tray A1. The biomaterial printing apparatus 1 can print a variety of biological materials in the culture container A2 to form a three-dimensional biomimetic product.

In the embodiment, the size and the number of the receiving groove A11 correspond to the size and the number culture container A2. Moreover, the size and the number of the culture container A2 should not be limited. In some embodiments, the number of the culture container A2 is in a range from 1 to 100, but it is not limited thereto. The greatest width of the culture container A2 is in a range from 1 cm to 10 cm, but it is not limited thereto. The width is measured in a direction parallel to a horizontal plane when the culture container A2 is put on a horizontal plane.

In some embodiments, the tray A1 may be excluded. The culture container A2 is directly disposed in the support groove 11 of the support base 10.

The movement device 20 is connected to the support base 10. The movement device 20 is configured to move the support base 10 and the printing device 30. The movement device 20 includes a platform 21, a Y-axis movement mechanism 22, an X-axis movement mechanism 23 and Z-axis movement mechanisms 24. The Y-axis movement mechanism 22 is disposed on the platform 21, and connected to the support base 10. The Y-axis movement mechanism 22 is configured to move the support base 10 in a Y direction.

In some embodiments, the support base 10 may be affixed to the platform 21. In other words, the support base 10 is not moved relative to the platform 21. The Y-axis movement mechanism 22 is disposed on the platform 21, and configured to move the X-axis movement mechanism 23 in the Y direction.

The X-axis movement mechanism 23 is disposed on the platform 21, and the Z-axis movement mechanisms 24 are movably disposed on the X-axis movement mechanism 23. The X-axis movement mechanism 23 is configured to move the Z-axis movement mechanisms 24 in an X direction. Moreover, the printing devices 30 are movably disposed on the Z-axis movement mechanisms 24. The Z-axis movement mechanisms 24 are configured to move the printing devices 30 in a Z direction.

Accordingly, in the embodiment, the printing device 30 can be moved relative to the support base 10 in the X direction and the Z direction by the X-axis movement mechanism 23 and the Z-axis movement mechanism 24. Moreover, the support base 10 can be moved relative to the printing device 30 in the Y direction by the Y-axis movement mechanism 22. In other words, the printing device 30 can be moved relative to the support base 10 in three axial directions (X direction, Y direction and Z direction).

Figure 2A:
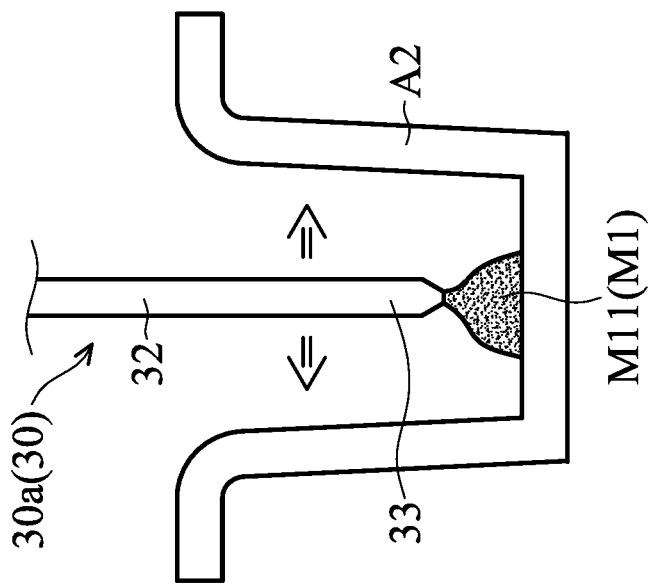
FIGS. 2A, 2B and 2C are schematic views of the culture containers during an intermediate stage of the printing process in accordance with some embodiments of the present disclosure.
Figure 2B:
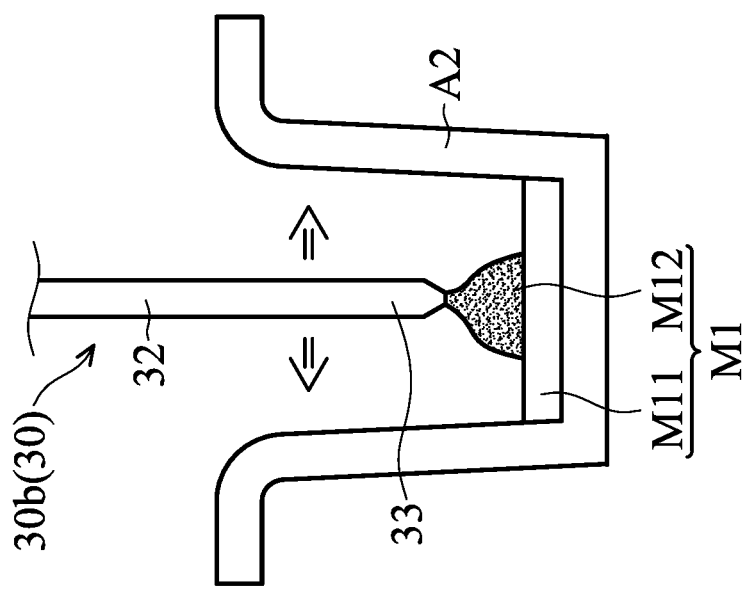
Figure 2C:
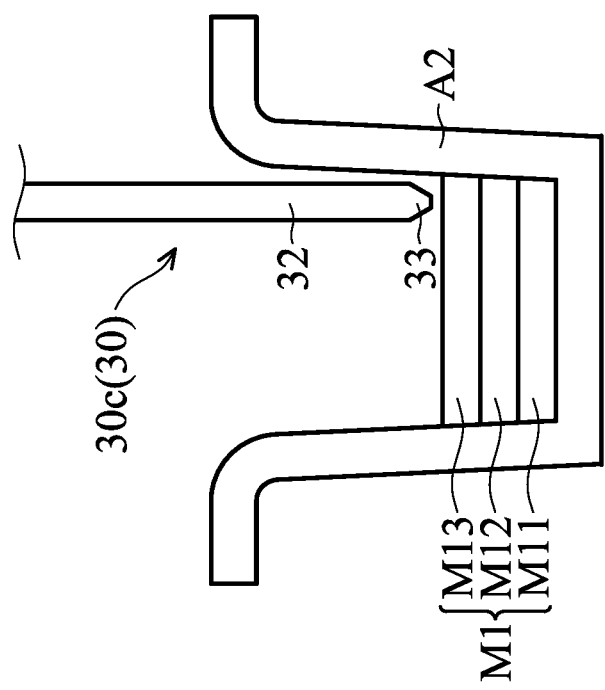

Each of the printing devices 30 includes an injector 31 and an injection needle 32. The injector 31 is configured for receiving biological materials M1 (as shown in FIGS. 2A, 2B and 2C). The injection needle 32 is connected to the injector 31. The biological material M1 in the injector 31 can flow out via the needle head 33 of the injection needle 32.

FIGS. 2A, 2B and 2C are schematic views of the culture containers A2 during an intermediate stage of the printing process in accordance with some embodiments of the present disclosure. As shown in FIGS. 1 and 2A, the injection needle 32 can be moved to an injection position relative to the culture container A2 by the movement device 20. The printing device 30 can inject the biological material M1 in the injector 31 into the culture container A2 via the needle head 33 of the injection needle 32.

In order to evenly distribute the biological material M1 to the culture container A2, the movement device 20 can move the injection needle 32 from the injection position along the injection path relative to the culture container A2. The injection path may be a spiral path on the horizontal plane. The injection position is located at the center of the culture container A2, and the injection needle 32 moves along the spiral path from the center of the culture container A2 towards the side wall of the culture container A2. In some embodiments, the injection needle 32 moves along the spiral path from the side wall of the culture container to the center. In some embodiments, Injection needle 32 moves along a bending path including linear segments, and the bending path is located on a horizontal plane.

The biological material M1 may include biological material M11, biological material M12, and biological material M13. In FIG. 2A, the printing device 30a prints the biological material M11 in the culture container A2. After the printing device 30a prints the biological material M11, in FIG. 2B, the movement device 20 moves another printing device 30b to the injection position of the culture container A2, and stars printing the biological material M12. In FIG. 2C, the printing device 30c had print the biological material M13, and The movement device 20 moves the printing device 30c away from the culture container A2, and the printing of three-dimensional biomimetic product is completed.

Accordingly, the biomaterial printing apparatus 1 of the present disclosure can utilize the movement device 20 and the printing device 30 to perform three-dimensional printing of the biomimetic product, thereby reducing the difficulty of producing the biomimetic product.

In the embodiment, the biomimetic product includes three different biological materials M1, but it is not limited thereto. In other embodiments, the biomimetic product includes at least one or two different biological materials M1. For example, the biomimetic product includes one, two, four, or more than five different biological materials M1.

In the embodiment, the biomimetic product may be bionic skin. For the purpose of clarity, in the embodiment, there are three different biological materials M11, M12 and M13 disclosed. For example, the biological material M11 may be collagen. The biological material M12 may be biodegradable polymer materials, such as polylactide (PLA) or polycaprolactone (PCL). The biological material M13 may be human fibroblasts, human epidermal cells or biological cells.

Moreover, for the purpose of clarity, in FIG. 2C, one layer of biological material M11, one layer of biological material M12 and one layer of biological material M13 are drawn. In some embodiments, there are many layers of biological material M11, biological material M12 and/or biological material M13, and the layers may be alternately arranged.

When making a biomimetic product, the parameters such as the thickness of each biological material M1 need to be controlled very precisely to produce a good quality biomimetic product. Therefore, the position of each culture container A2 relative to the support base 10, the position of the needle head 33 of the injection needle 32 of each printing device 30, and the height of the biological material M1 within the culture container A2 need to be very precisely controlled and calibrated. In the embodiment, the biomaterial printing apparatus 1 utilizes multiple optical-detection devices for detection and calibration, which in turn improves the yield of the biomimetic product.

Figure 3:
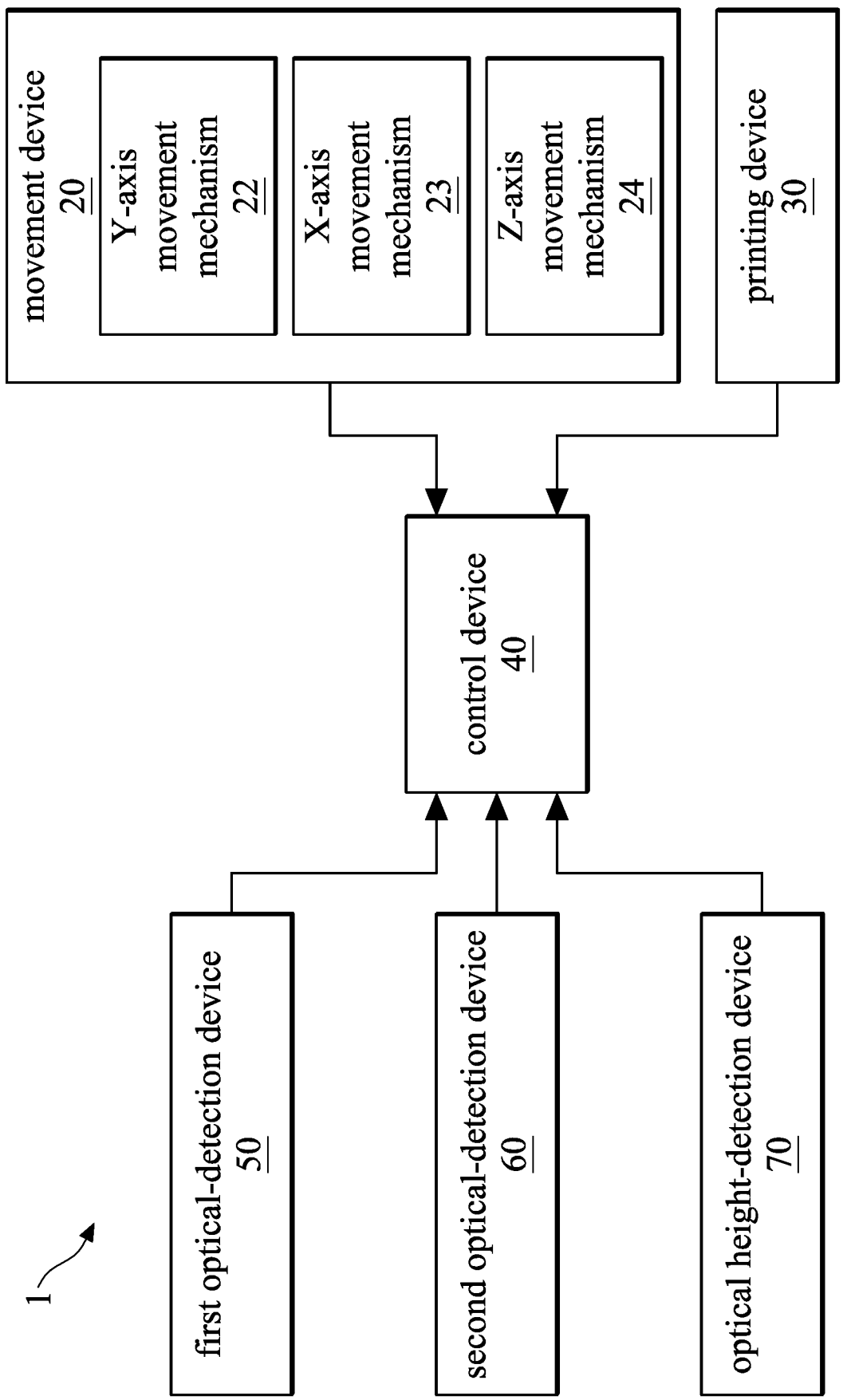
FIG. 3 is a system diagram of the biomaterial printing apparatus in accordance with some embodiments of the present disclosure.

FIG. 3 is a system diagram of the biomaterial printing apparatus 1 in accordance with some embodiments of the present disclosure. In the embodiment, the biomaterial printing apparatus 1 further includes a control device 40, a first optical-detection device 50, a second optical-detection device 60, and an optical height-detection device 70. The control device 40 may be electrically connected to the movement device 20, the printing device 30, a first optical-detection device 50, a second optical-detection device 60, and an optical height-detection device 70.

The control device 40 may be a computer. The control device 40 is configured to control the movement of the Y-axis movement mechanism 22, the X-axis movement mechanism 23, and the Z-axis movement mechanism 24 of the movement device 20. Moreover, the control device 40 may control the flow of the printing device 30 to the biological material M1 via the injection needle 32.

In the embodiment, the first optical-detection device 50 can correct the position of the needle head 33 of the injection needle 32, and the second optical-detection device 60 can measure the position of the culture container A2 relative to the support base 10. Moreover, the optical height-detection device 70 can detect the height of the top surface of the biological material M1 in the culture container A2. Therefore, the printing device 30 can accurately print the biological material M1 into the culture container A2, thereby increasing the yield of the biomimetic product.

The first optical-detection device 50 may be connected to the support base 10, and electrically connected to the control device 40. In some embodiments, the first optical-detection device 50 may be disposed on the platform 21. The first optical-detection device 50 is configured to detect the position of the needle head 33 of the injection needle 32, and generate a first detection signal, and transmits the first detection signal to the control device 40.

Figure 4:
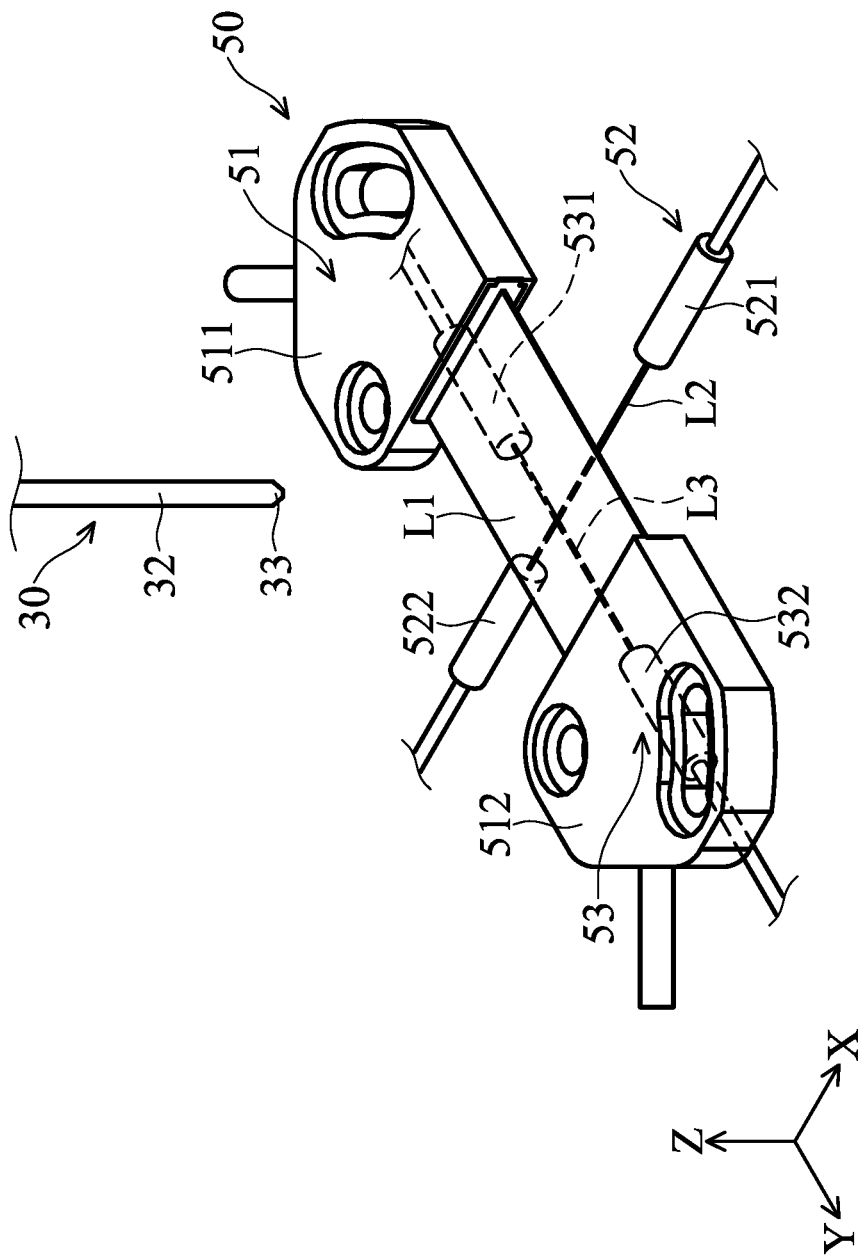
FIG. 4 is a perspective view of the first optical-detection device in accordance with some embodiments of the present disclosure.

FIG. 4 is a perspective view of the first optical-detection device 50 in accordance with some embodiments of the present disclosure. FIGS. 5A, 5B, 5C and 5D are schematic views of the first optical-detection device 50 during a calibration process in accordance with some embodiments of the present disclosure. In the embodiment, the first optical-detection device 50 includes a Z-axis detection module 51, an X-axis detection module 52, and a Y-axis detection module 53. The Z-axis detection module 51 is configured to generate a Z-axis detection beam L1. In the embodiment, the Z-axis detection beam L1 is a plane beam transmitting in a horizontal plane.

The Z-axis detection module 51 may include a Z-axis beam emitter 511 and a Z-axis beam receiver 512. The Z-axis beam emitter 511 is configured to emit a Z-axis detection beam L1. The Z-axis beam receiver 512 is configured to receive the Z-axis detection beam L1, and generate a Z-axis detection signal according to the received Z-axis detection beam L1.

The X-axis detection module 52 is configured to generate an X-axis detection beam L2. In the embodiment, the X-axis detection beam L2 is a linear beam transmitting in the X direction. The X-axis detection module 52 includes an X-axis beam emitter 521 and an X-axis beam receiver 522. The X-axis beam emitter 521 is configured to emit an X-axis detection beam L2. The X-axis beam receiver 522 is configured to receive the X-axis detection beam L2, and generate an X-axis detection signal according to the received X-axis detection beam L2.

The Y-axis detection module 53 is configured to generate a Y-axis detection beam L3. In the embodiment, Y-axis detection beam L3 is a linear beam transmitting in the Y direction. Y-axis detection module 53 includes a Y-axis beam emitter 531 and a Y-axis beam receiver 532. The Y-axis beam emitter 531 is configured to emit a Y-axis detection beam L3. The Y-axis beam receiver 532 is configured to receive the Y-axis detection beam L3, and generate a Y-axis detection signal according to the received Y-axis detection beam L3. In the embodiment, the X direction is perpendicular to the Y direction, and the X direction and the Y direction are parallel to the horizontal plane.

In some embodiments, the X-axis beam emitter 521, the X-axis beam receiver 522, the Y-axis beam emitter 531 and the Y-axis beam receiver 532 are located on a first reference plane P1. The X-axis detection beam L2 and the Y-axis detection beam L3 may be transmitted in the first reference plane P1, and pass through the central axis AX1. The first reference plane P1 may be a horizontal plane. The central axis AX1 may be perpendicular to the first reference plane P1, the X direction and the Y direction.

The Z-axis beam emitter 511 and the Z-axis beam receiver 512 may be located on a second reference plane P2. The Z-axis detection beam L1 may be transmitted in the second reference plane P2, and may pass through the central axis AX1. The second reference plane P2 may be parallel to the first reference plane P1, and separated from the first reference plane P1. In the embodiment, in the Z direction, the second reference plane P2 is located on the first reference plane P1.

Figure 5A:
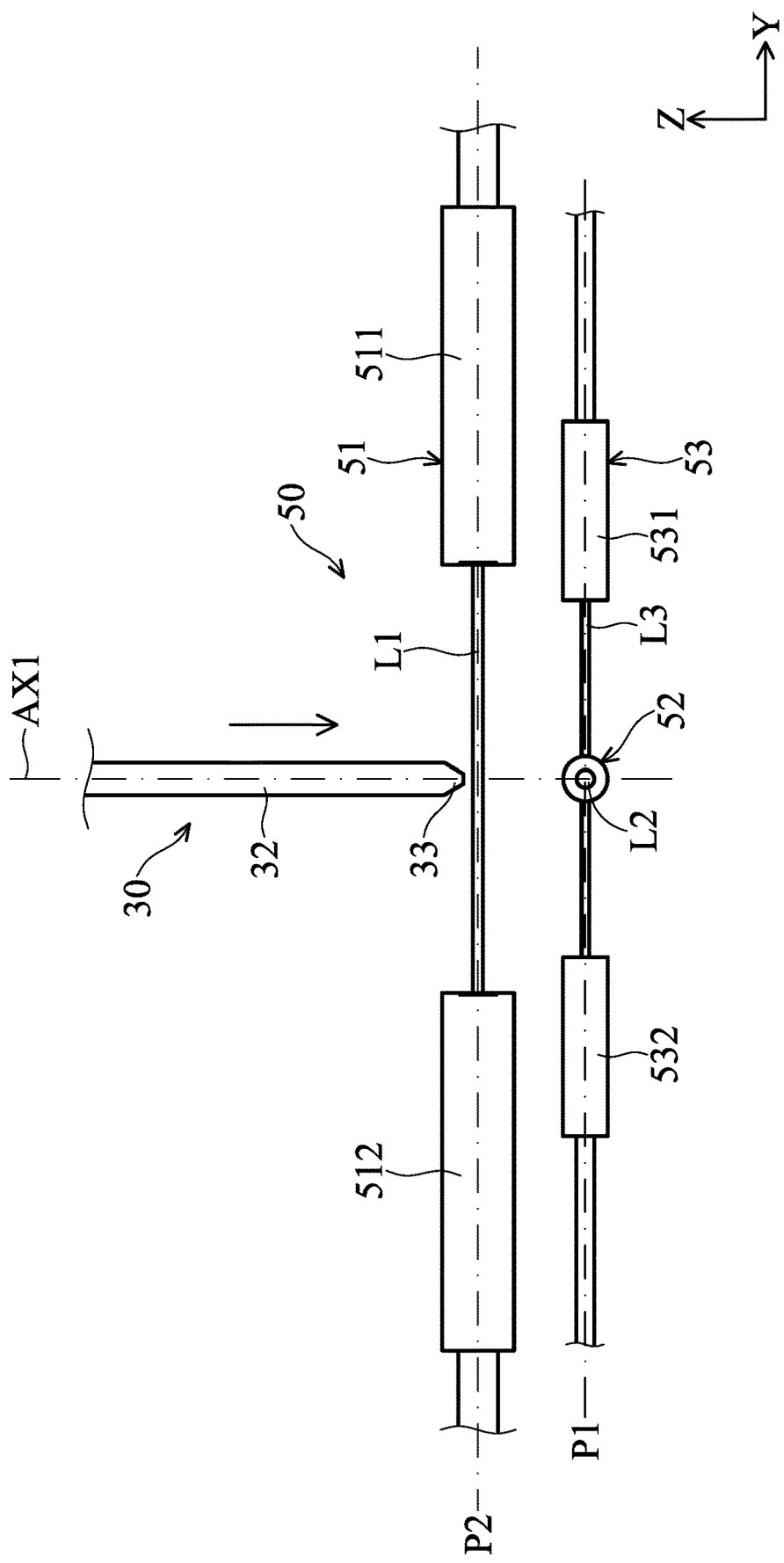
FIGS. 5A, 5B, 5C and 5D are schematic views of the first optical-detection devices during a calibration process in accordance with some embodiments of the present disclosure.

As shown in FIG. 5A, when the injection needle 32 is calibrated using the first optical-detection device 50, the control device 40 drives the movement device 20 to move the injection needle 32 to a detection position. If the position of the injection needle 32 is not offset, the injection needle 32 extends downwardly along the central axis AX1, and the central axis AX1 may pass through the center of the injection needle 32 and the needle head 33. In other words, the injection needle 32 is not inclined relative to the central axis AX1.

Afterward, the movement device 20 further downwardly moves the injection needle 32 in the Z direction. When the needle head 33 of the injection needle 32 shields a portion of the Z-axis detection beam L1, the Z-axis detection module 51 generates a Z-axis detection signal, and transmits the Z-axis detection signal to the control device 40. The control device 40 drives the movement mechanism 24 to downwardly move the injection needle 32 in the Z direction by a predetermined distance according to the Z-axis detection signal, so as to move the needle head 33 to the first reference plane P1.

Figure 5B:
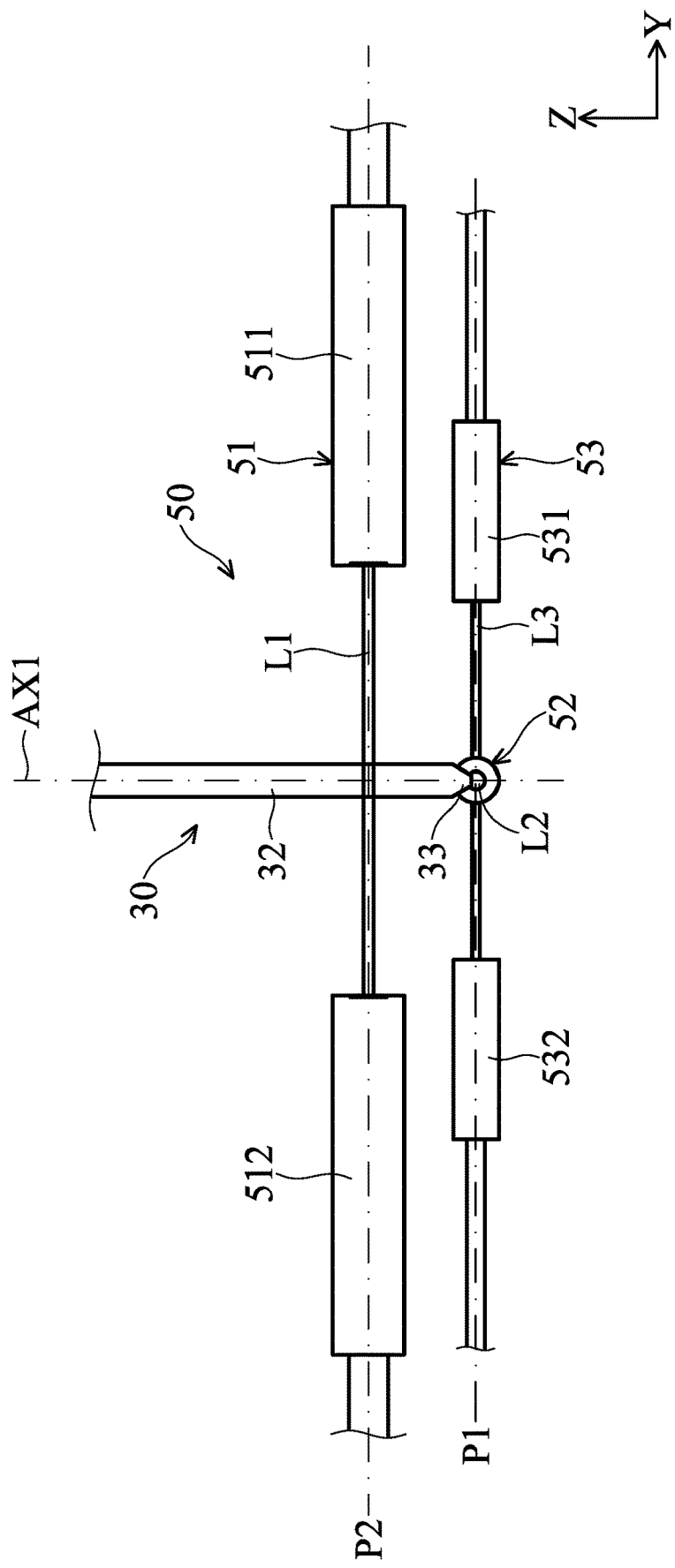

As shown in FIG. 5B, if the position of the injection needle 32 is not offset, the needle head 33 on the first reference plane P1 and the central axis AX1 will simultaneously shield the X-axis detection beam L2 and the Y-axis detection beam L3. The control device 40 determines that the injection needle 32 does not deviate, and the needle of the injection needle 32 is located in a standard position relative to the printing device 30.

Figure 5C:
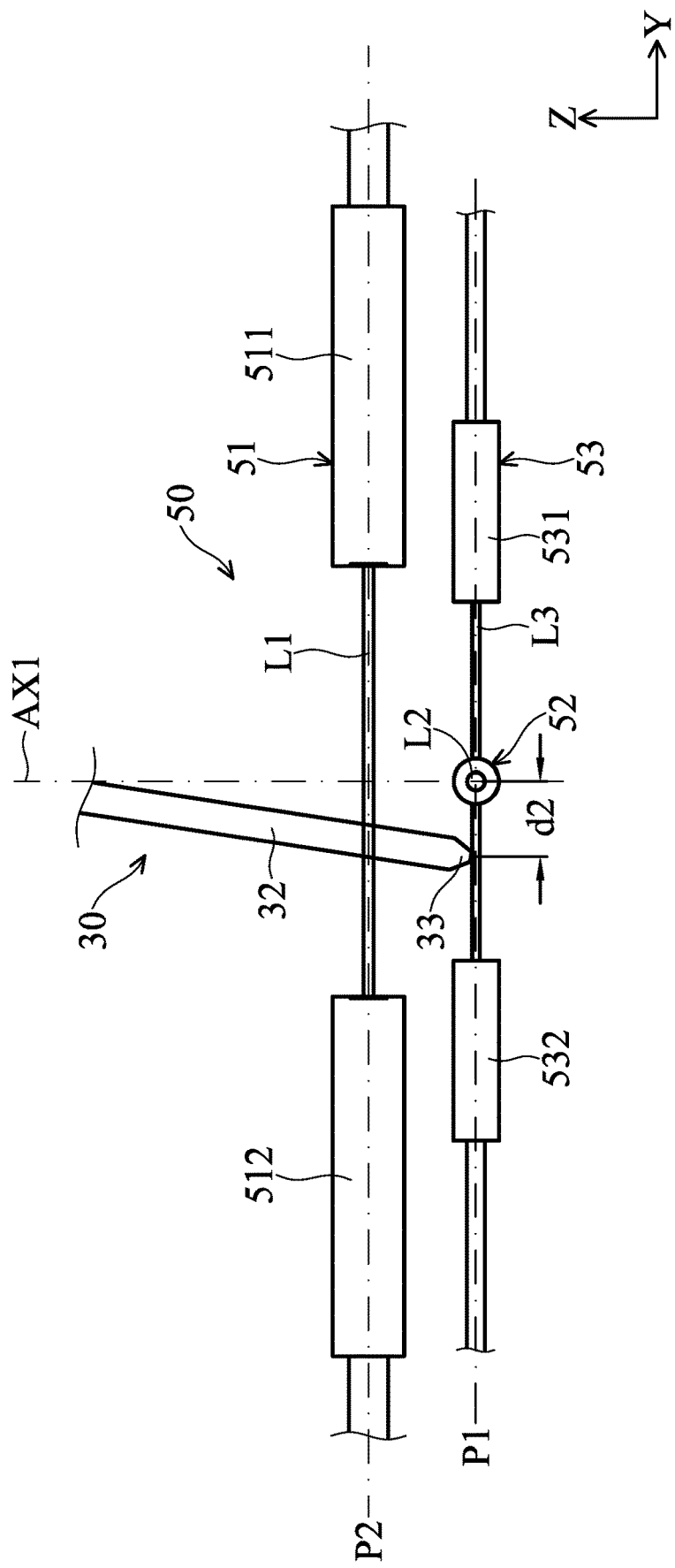
Figure 5D:
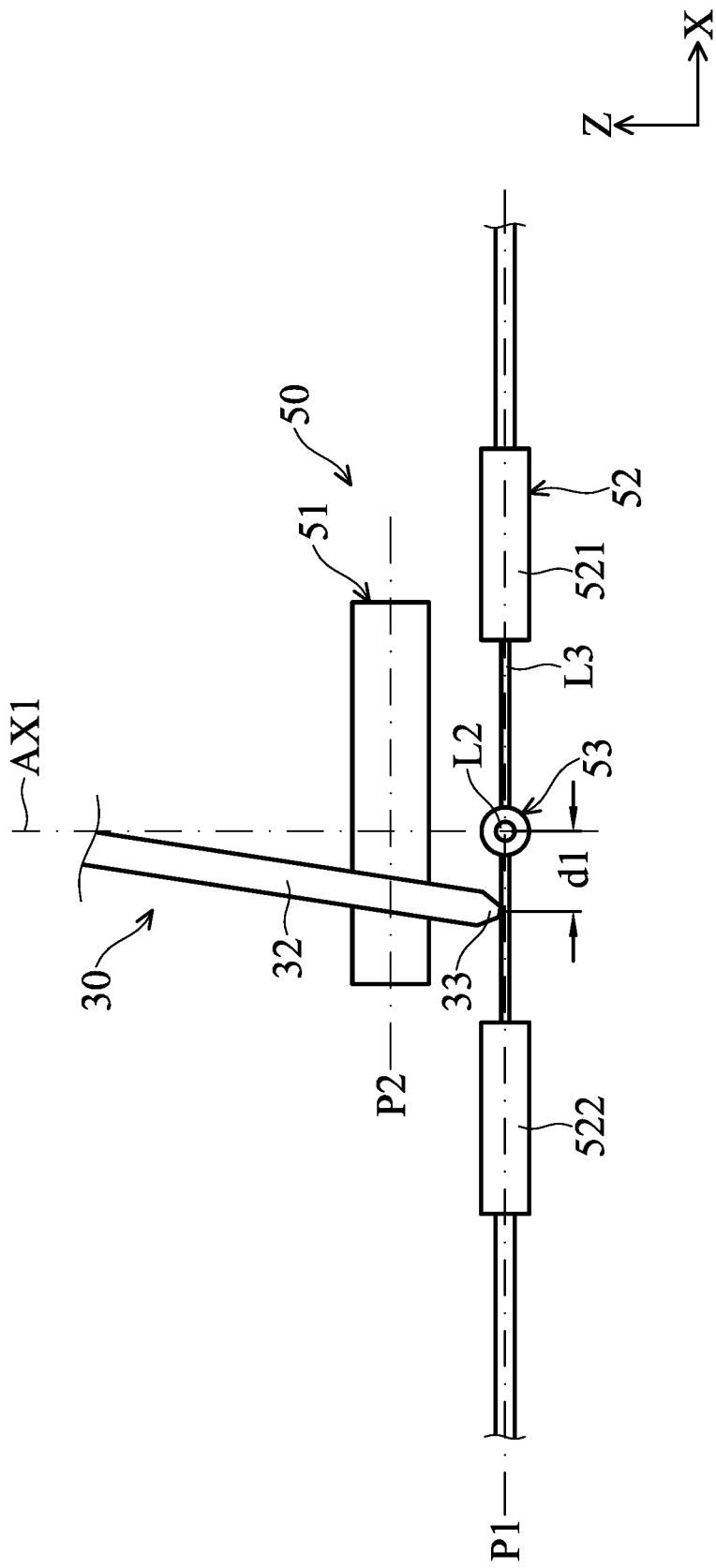

As shown in FIGS. 5C and 5D, if the position of the injection needle 32 is offset, the needle head 33 located in the first reference plane P1 does not simultaneously shield the X-axis detection beam L2 and/or the Y-axis detection beam L3. Moreover, the control device 40 drives the movement device 20 to move an X-axis offset distance d1 in the X direction until the needle head 33 shields the X-axis detection beam L2, and the X-axis detection module 52 generates an X-axis detection signal.

After, the control device 40 drives the movement device 20 moves a Y-axis offset distance d2 in Y direction until the needle head 33 shields the Y-axis detection beam L3, and the Y-axis detection module 53 generates a Y-axis detection signal.

The first detection signal includes the Z-axis detection signal, the X-axis detection signal, the Y-axis detection signal, the X-axis offset distance d1 and the Y-axis offset distance d2. Moreover, the first detection signal is transmitted to the control device 40.

The control device 40 obtains the offset position of the needle head 33 according to the first detection sign. The control device 40 can correct the position of the needle head 33 according to the standard position and the offset position, so that the injection needle 32 can accurately inject the biological material M1 into the culture container A2.

In the embodiment, the X-axis detection beam L2 and the Y-axis detection beam L3 are located on the first reference plane P1. However, In some embodiments, the X-axis detection beam L2 and the Y-axis detection beam L3 are respectively located in two planes parallel to and separated from the first reference plane P1. The first optical-detection device 50 can shield the X-axis detection beam L2 and the Y-axis detection beam L3 by the needle head 33 of the injection needle 32 to detect the needle head 33 of the injection needle 32 and generate the first Detection signal.

Figure 6:
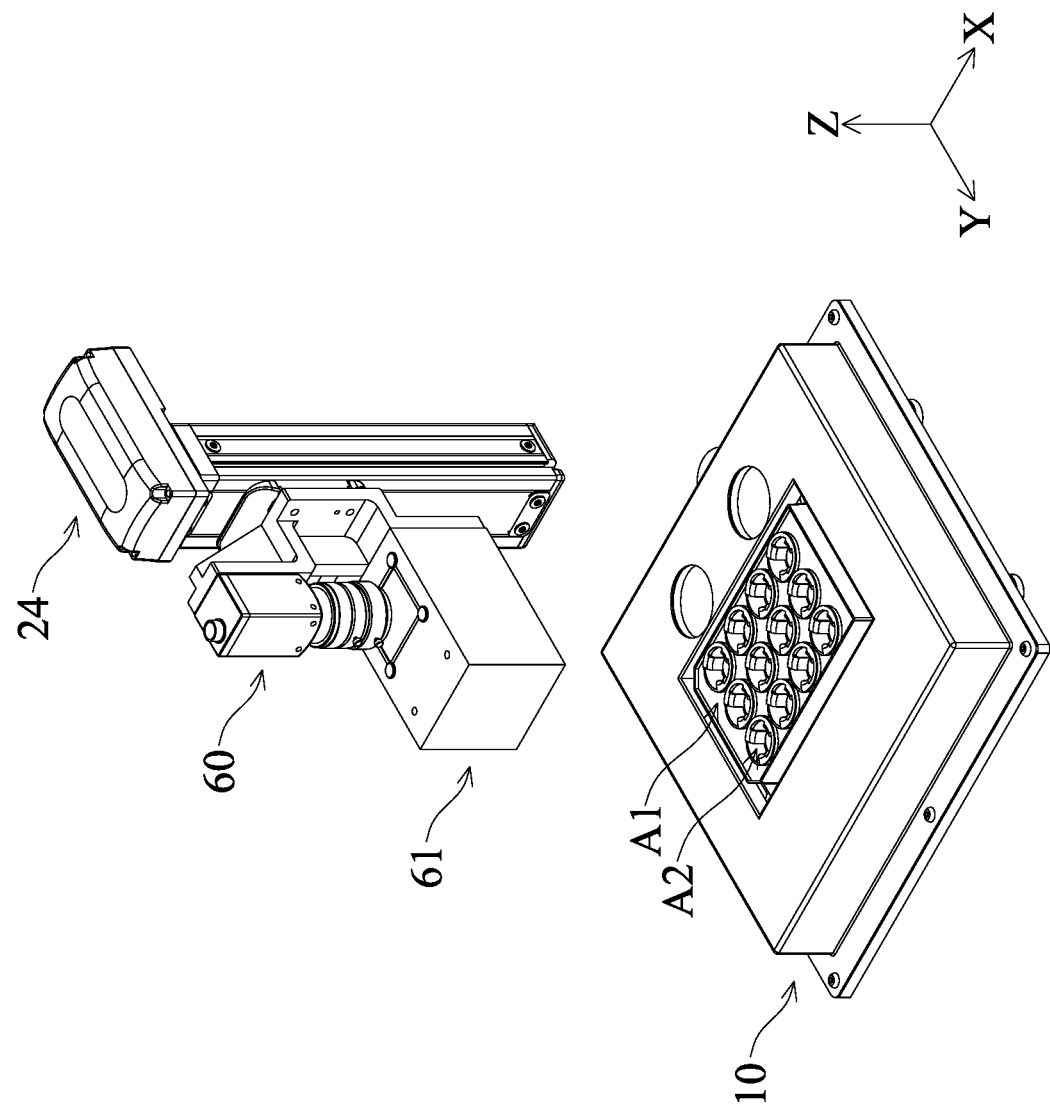
FIG. 6 is a perspective view of the second optical-detection device in accordance with some embodiments of the present disclosure.
Figure 7:
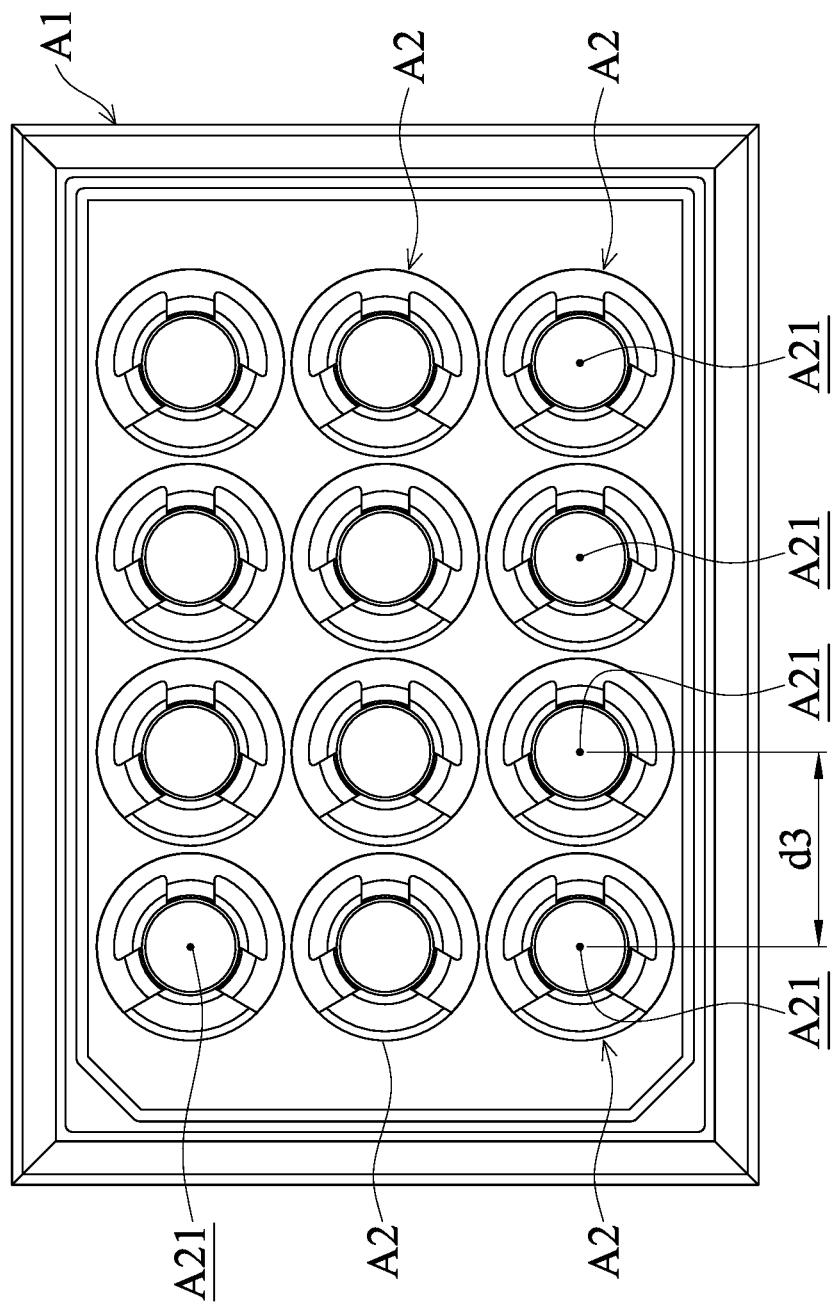
FIG. 7 is a top view of the tray and the culture container in accordance with some embodiments of the present disclosure.

FIG. 6 is a perspective view of the second optical-detection device 60 in accordance with some embodiments of the present disclosure. FIG. 7 is a top view of the tray A1 and the culture container A2 in accordance with some embodiments of the present disclosure. The second optical-detection device 60 may be movably disposed on the Z-axis movement mechanism 24 of the movement device 20. The second optical-detection device 60 is configured to detect the position of the culture container A2, generate a second detection signal, and transmit the second detection signal to the control device 40.

In the embodiment, the second optical-detection device 60 includes a camera module 61 configured to capture an image of the culture container A2 to form a second detection signal. In the embodiment, the second detection signal may be an image signal. The control device 40 drives the movement device 20 the second optical-detection device 60 above the culture container A2, and capture the image of the culture container A2. Moreover, the control device 40 drives the Z-axis movement mechanism 24 to move the camera module 61 in the Z direction in order to make the camera module 61 focus on the culture container A2.

The control device 40 calculates a center coordinate of the center A21 of each culture container A2 according to the image signal (second detection signal), and calculates an injection position of the center coordinate. The control device can calculate the spacing d3 of two adjacent culture containers A2 according to the coordinates of the centers A21 of the two adjacent culture containers A2 (as shown in FIG. 7).

Accordingly, the control device 40 may drive the movement device 20 according to the offset position to precisely move the injection needle 32 to the injection position, and drive the printing device 30 to inject the biological material M1 into the culture container A2 via the injection needle 32. Therefore, the injection needle 32 can accurately inject the biological material M1 into the culture container A2.

After the printing device 30 prints the biological material M1 in one culture container A2, the control device 40 can move the injection needle 32 to the injection position of next culture container A2 according to the spacing d3. In some embodiments, after the printing device 30 prints the biological material M1 in one culture container A2, the control device 40 can move the injection needle 32 to the injection position of next culture container A2 according to a center coordinate of the next culture container A2. Accordingly, the control device 40 can accurately move the injection needle 32 to the injection position of each culture container A2 to prevent the deviation of the position of the biological material M1 when the culture container A2 is offset.

Figure 8:
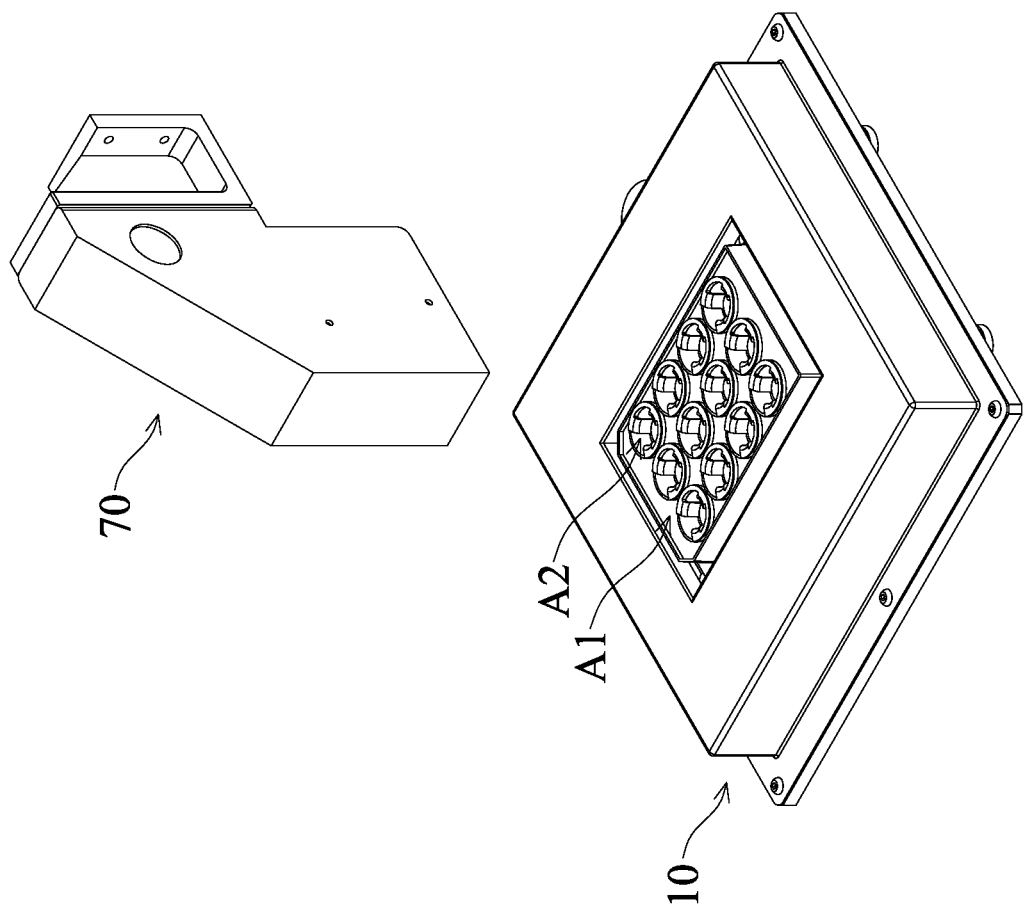
FIG. 8 is a perspective view of the optical height-detection device in accordance with some embodiments of the present disclosure.
Figure 9:
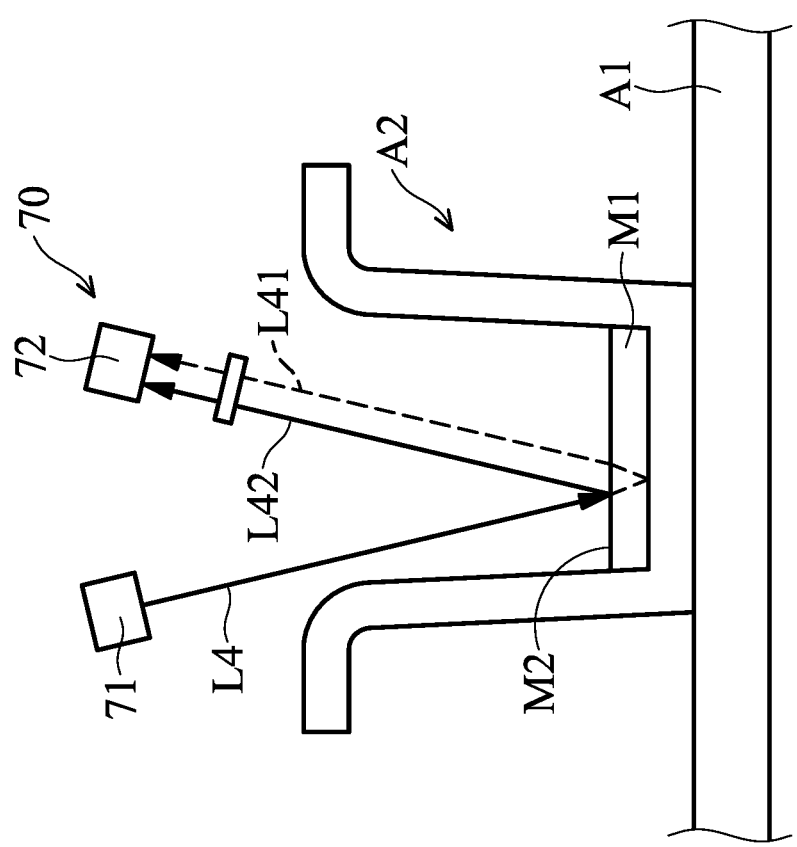
FIG. 9 is a schematic view of the optical height-detection device in accordance with some embodiments of the present disclosure.

FIG. 8 is a perspective view of the optical height-detection device 70 in accordance with some embodiments of the present disclosure. FIG. 9 is a schematic view of the optical height-detection device 70 in accordance with some embodiments of the present disclosure. The optical height-detection device 70 may be disposed on the Z-axis movement mechanism 24 or the X-axis movement mechanism 23 of the movement device 20. The optical height-detection device 70 is configured to detect the height of the top surface M2 of the biological material M1 in the culture container A2, and generate a height-detection signal. The control device 40 may calculate the injection position according to a center coordinate and the height-detection signal.

The optical height-detection device 70 includes a height-beam emitter 71 and a height-beam receiver 72. The height-beam emitter 71 is configured to emit a height-detection beam L4 toward the bottom of the culture container A2. The height-beam receiver 72 is configured to the receive height-detection beam L4 reflected by the bottom of the culture container A2. In the embodiment, the optical height-detection device 70 may be a laser range finder. The height-detection beam L4 may be a laser beam.

As shown in FIG. 9, a portion of the height-detection beam L41 may be reflected to the height-beam receiver 72 by the culture container A2, and a portion of the height-detection beam L42 may be reflected to the height-beam receiver 72 by the top surface M2 of the biological material M1 in the culture container A2. The optical height-detection device 70 generates a height-detection signal according to the position of the height-detection beam L41 and the height-detection beam L42 falling on the height-beam receiver 72. The control device 40 calculates the height of the top surface M2 of the biological material M1 relative to the bottom of the culture container A2 according to the height-detection signal, and generates height data.

In the embodiment, the control device 40 may calculate the injection position according to the height data and the center coordinate. In the embodiment, the injection position is higher than a predetermined height of the top surface M2 of the biological material M1 in the Z direction. In some embodiments, the predetermined height is in a range from about 0.1 mm to 5 mm. Accordingly, the optical height-detection device 70 allows the injection needle 32 to move more accurately to the injection position and allows the biological material M1 to be injected more accurately into the culture container A2.

Figure 10:
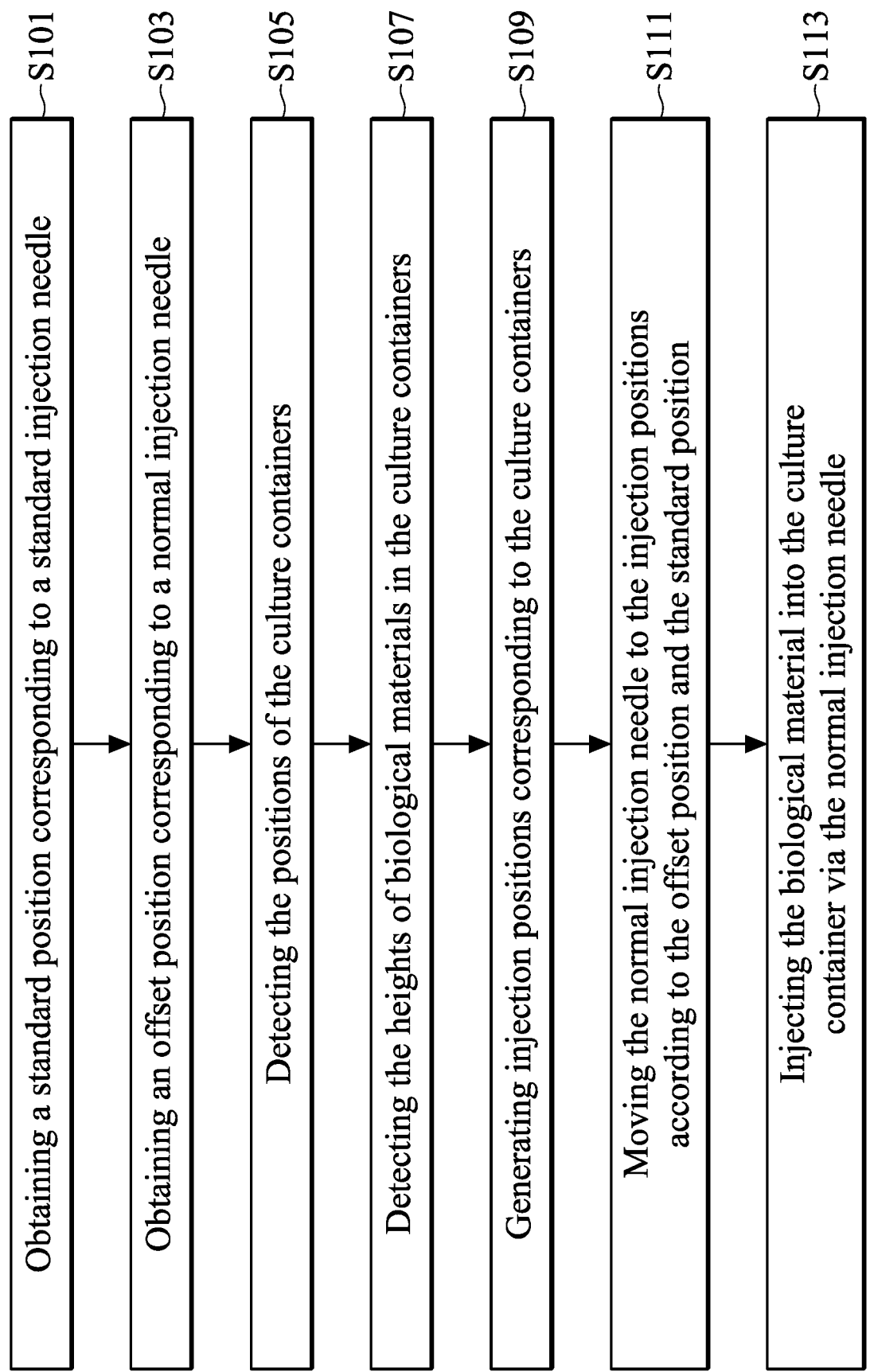
FIG. 10 is a flow chart of an operation method of the biomaterial printing apparatus in accordance with some embodiments of the present disclosure.

FIG. 10 is a flow chart of an operation method of the biomaterial printing apparatus 1 in accordance with some embodiments of the present disclosure. The disclosed features may be combined, modified, or replaced in any suitable manner in one or more disclosed embodiments, but are not limited to any particular embodiments.

In step S101, the control device 40 drives the movement device 20 move a standard injection needle 32 to a location above the first optical-detection device 50. The first optical-detection device 50 detects the standard injection needle 32 (as shown in FIGS. 4A and 4B), and generate a first detection signal. The control device 40 obtains a standard position corresponding to the standard injection needle according to the first detection signal.

In the embodiment, when the control device 40 moves the standard injection needle 32 to the injection position, the needle head 33 of the standard injection needle 32 is located over the center A21 of the culture container A2 in the Z direction. Moreover, after the standard position is obtained, the standard injection needle 32 may be replaced by a normal injection needle 32.

In step S103, the control device 40 drives the movement device 20 to move the normal injection needle 32 to a located above the first optical-detection device 50. The first optical-detection device 50 detects the normal injection needle 32, and generates a first detection signal. The control device 40 obtains an offset position corresponding to the normal injection needle 32 according to the first detection signal.

In step S105, the second optical-detection device 60 detects the position of each culture container A2. In the embodiment, the control device 40 drives the movement device 20 to move the second optical-detection device 60 to a location above the culture container A2. The control device 40 drives the second optical-detection device 60 to detect the culture container A2 and generate a second detection signal. The control device 40 analyzes the second detection signals, and calculates a center coordinate of each culture container A2.

In step S107, when the biological material M1 is in the culture container A2, the optical height-detection device 70 detect the height of the top surface M2 of the biological material M1 relative to the bottom of the culture container A2 of each culture container A2. In the embodiment, the control device 40 drives the movement device 20 to move the optical height-detection device 70 to a located above the culture container A2. The control device 40 drives the optical height-detection device 70 to detect the culture container A2 and generate a height-detection signal. The control device 40 analyses the height-detection signal, and generates height data.

In step S109, the control device 40 generate injection positions corresponding to the culture containers A2 according to the center coordinate and/or the height data. In step S111, the control device 40 drives the movement device 20 to move the injection needle 32 to the injection position according to the offset position of the needle head 33 and the standard position.

In step S113, the control device 40 drives the printing device 30 to inject the biological material M1 into the culture container A2 via the injection needle 32. Repeating step S113, the control device 40 drives the printing device 30 to move to the injection position of another culture container A2, and the biological material M1 is injected into the culture container A2 via the injection needle 32 until all of the culture containers A2 are filled by the biological materials M1.

The steps S103 to S113 may be repeatedly performed to inject different biological materials M1 into each culture container A2, so as to complete the printing of the three-dimensional biomimetic product.

In conclusion, the biomaterial printing apparatus of the present disclosure can produce a biomimetic product in a three-dimensional printing manner, thereby reducing the difficulty in the production of the biomimetic product. Moreover, the biomaterial printing apparatus of the present disclosure utilizes a variety of optical-detection devices, so that the injection needle can accurately inject the biological material into the culture container, thereby increasing the yield of the biomimetic product, and reducing the manufacturing cost of the biomimetic product.

While the present disclosure has been described by way of example and in terms of preferred embodiment, it should be understood that the present disclosure is not limited thereto. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A biomaterial printing apparatus, comprising:
   a support base configured for a least one culture container to be put thereon;
   at least one printing device comprising an injection needle that is configured for containing a biological material;
   a movement device configured to move the support base and the printing device;
   a control device electrically connected to the movement device and the printing device;
   a first optical-detection device electrically connected to the control device, wherein the first optical-detection device is configured to detect a position of the injection needle, generate a first detection signal, and transmit the first detection signal to the control device; and
   a second optical-detection device electrically connected to the control device, wherein the second optical-detection device is configured to detect a position of the culture container, generate a second detection signal, and transmit the second detection signal to the control device;
   wherein the control device drives the movement device to move the injection needle to an injection position according to the first detection signal and the second detection signal, and drives the printing device to inject the biological material into the culture container via the injection needle;

wherein the second optical-detection device is disposed on the movement device, and comprises a camera module, wherein the camera module is configured to take an image of the culture container and generate the second detection signal; and wherein the control device generates a center coordinate of the culture container according to the second detection signal, and the control device calculates the injection position according to the coordinate of the container center.

2. The biomaterial printing apparatus as claimed in claim 1, wherein the first optical-detection device comprises:
a Z-axis detection module configured to generate a Z-axis detection beam;
an X-axis detection module configured to generate an X-axis detection beam;
a Y-axis detection module configured to generate a Y-axis detection beam;
wherein when the injection needle passes through the Z-axis detection beam, the Z-axis detection module generates a Z-axis detection signal, when the injection needle passes through the X-axis detection beam, the X-axis detection module generates an X-axis detection signal, and when the injection needle passes through the Y-axis detection beam, the Y-axis detection module generates a Y-axis detection signal,
wherein the Z-axis detection signal, the X-axis detection signal and the Y-axis detection signal form the first detection signal.

3. The biomaterial printing apparatus as claimed in claim 2, wherein the Z-axis detection beam is a plane beam transmitting in a horizontal plane, the X-axis detection beam is a linear beam transmitting in an X direction, and the Y-axis detection beam is a linear beam transmitting in a Y direction, wherein the X direction is perpendicular to the Y direction, and the X direction and the Y direction are parallel to the horizontal plane.

4. The biomaterial printing apparatus as claimed in claim 1, further comprising an optical height-detection device configured to detect a height of a top surface of the biological material in the culture container, and generate a height-detection signal, wherein the control device drives the movement device to move the injection needle to the injection position according to the first detection signal, the second detection signal and the height-detection signal.

5. The biomaterial printing apparatus as claimed in claim 4, wherein the optical height-detection device comprises:
a height-beam emitter configured to emit a height-detection beam toward a bottom of the culture container; and
a height-beam receiver configured to receive the height-detection beam that is reflected by the bottom of the culture container and the top surface of the biological material.

6. The biomaterial printing apparatus as claimed in claim 1, wherein the movement device further comprises a Y-axis movement mechanism connected to the support base, and configured to move the support base in a Y direction.

7. The biomaterial printing apparatus as claimed in claim 1, wherein the movement device further comprises:
an X-axis movement mechanism; and
a plurality of Z-axis movement mechanisms disposed on the X-axis movement mechanism, and the printing device and the second optical-detection device are disposed on the Z-axis movement mechanisms,
wherein the X-axis movement mechanism is configured to move the Z-axis movement mechanisms in an X direction, and the Z-axis movement mechanisms are configured to move the printing device and the second optical-detection device in a Z direction.

8. The biomaterial printing apparatus as claimed in claim 1, wherein the biological material comprises collagen, biodegradable polymer material, human fibroblast, human epidermal cell, or biological cell.

* * * * *